United States Patent [19]

Wedekamp

[11] Patent Number: 4,948,980
[45] Date of Patent: Aug. 14, 1990

[54] APPARATUS FOR IRRADIATING MEDIA WITH UV-LIGHT

[75] Inventor: Horst Wedekamp, Herford, Fed. Rep. of Germany

[73] Assignee: Wedeco Gesellschaft fur Entkeimungsanlagen m.b.H., Herford, Fed. Rep. of Germany

[21] Appl. No.: 383,322

[22] Filed: Jul. 20, 1989

[30] Foreign Application Priority Data

Jul. 20, 1988 [DE] Fed. Rep. of Germany ....... 3824647

[51] Int. Cl.$^5$ .............................................. A61L 2/00
[52] U.S. Cl. ........................... 250/504 R; 250/432 R; 250/435; 250/492.1; 250/455.1; 422/24
[58] Field of Search ............... 250/504 R, 432 R, 435, 250/492.1, 455.1; 422/24

[56] References Cited

U.S. PATENT DOCUMENTS

| | | | |
|---|---|---|---|
| 3,686,940 | 8/1972 | Kockott | 250/504 R |
| 4,309,616 | 1/1982 | Wolff | 250/504 R |
| 4,766,321 | 8/1988 | Lew et al. | 422/24 |
| 4,798,702 | 1/1989 | Tucker | 422/24 |
| 4,816,694 | 3/1989 | Kuppenheimer, Jr. et al. | 250/504 R |

*Primary Examiner*—Janice A. Howell
*Assistant Examiner*—Kiet T. Nguyen
*Attorney, Agent, or Firm*—Collard, Roe & Galgano

[57] ABSTRACT

Apparatus is provided for irradiating liquid or gases by means of UV-light, consisting of a tubular body through which the medium to be irradiated flows, and at lest two UV-light sources with reflectors arranged externally to the tubular body and having parallel axes. The UV-light sources are flat radiators facing the tubular body with their narrow sides.

9 Claims, 4 Drawing Sheets

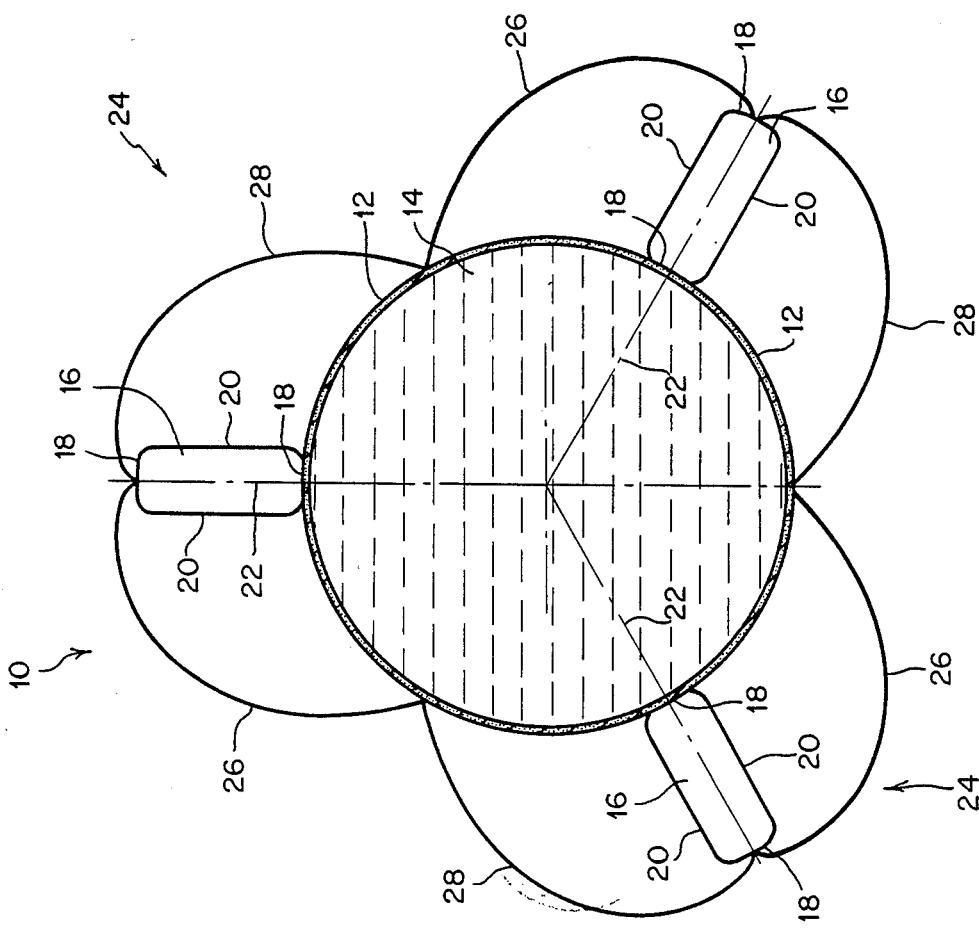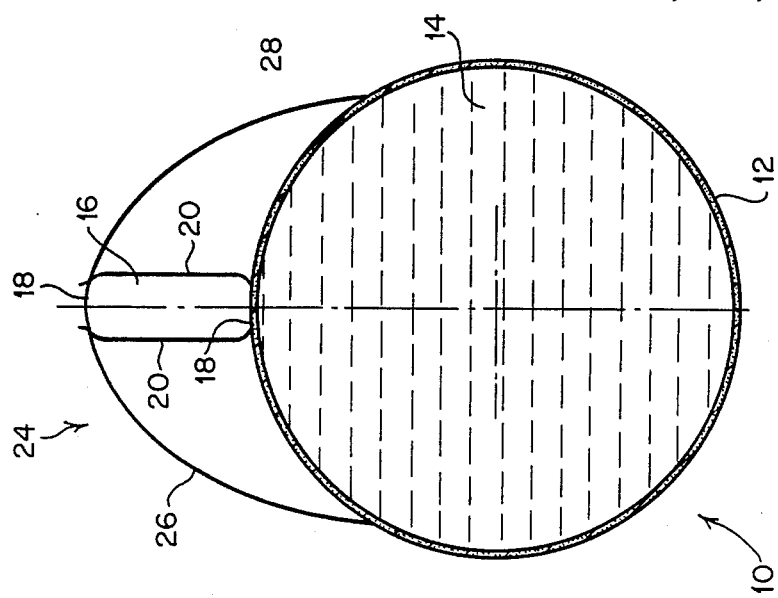

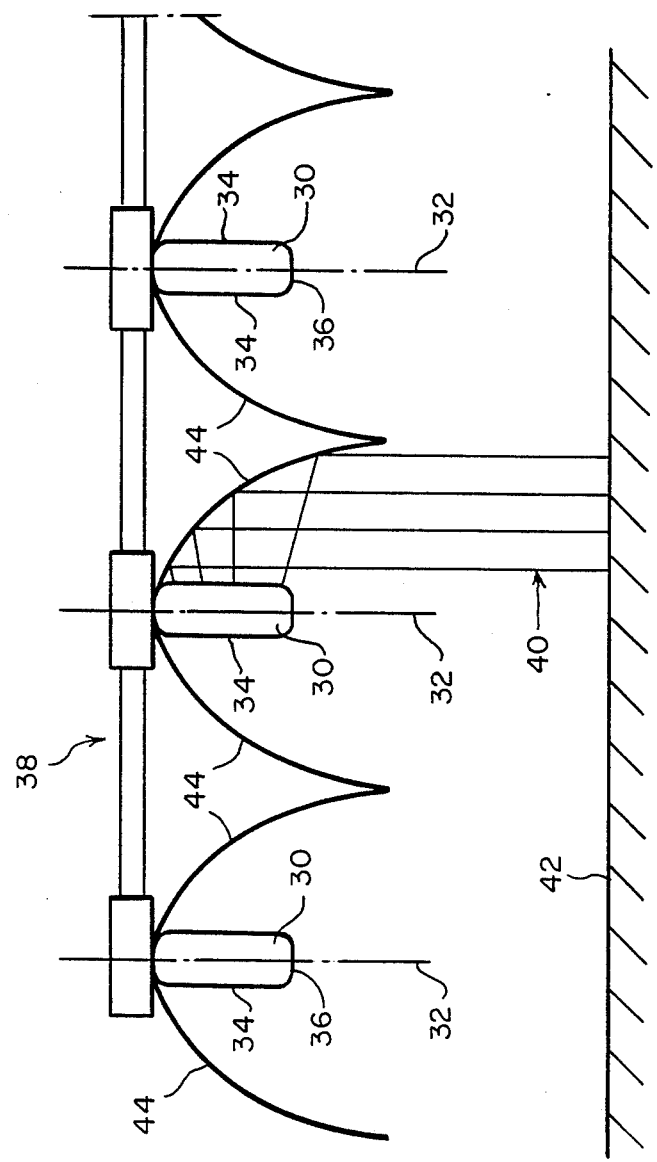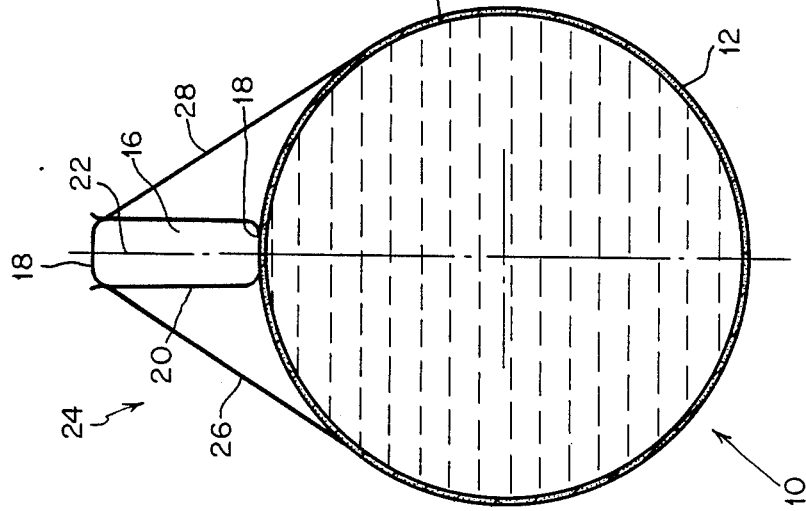

APPARATUS FOR IRRADIATING MEDIA WITH UV-LIGHT

The present invention relates to apparatus for irradiating media by means of UV-light, for example for the sterilization of liquids and/or gases by UV-light, wherein the UV-light sources are arranged axially parallel in the form of a ring around a tubular body according to the principle of the so-called positive irradiation geometry, and the medium flows through said tubular body.

In order to achieve the highest possible efficiency for UV-sterilization with the lowest expenditure in cost requires maximization of the irradiation intensities in the irradiation chamber. In order to achieve high irradiation intensities at every point of the irradiation chamber formed by a tubular body, it is known from German Patent No. 21 19 961 to conduct the medium to be sterilized through the tubular body, which is formed of quartz and is permeable to UV-light, wherein provision is made for a plurality of UV-light sources arranged externally to and axially parallel around the tubular body. In such arrangement, a reflector is associated with each light source in order that the highest possible radiation energy is made available for the medium flowing in the tubular body.

This type of arrangement of the light sources relative to the tubular body is noted for the fact that through focusing, the radiation intensity increases with an increase in distance from the radiation source. This type of irradiation has become known in the art as "positive irradiation geometry".

This previously known apparatus has proved its worth in practical applications. However, the low energy transfer in the tubular body of only about 55% is a drawback. A major part of the radiation emitted by the UV-light sources is lost in this apparatus by return reflection in the light sources, as well as by absorption.

It is an object of the present invention to improve the above described apparatus so as to achieve a significant increase in irradiation intensity, i.e., of the radiation density in the fluid to be treated, through optimized energy transfer and increased output.

The above object is accomplished in accordance with the present invention by providing an apparatus for irradiating media with UV-light consisting of a tubular body formed of UV-permeable material through which passes the media and at least two UV-light sources with reflectors arranged externally to the tubular body with axes parallel to each other, wherein the UV-light sources are flat UV-radiators having oblong, flat oval cross-sections with wide and narrow sides.

The present invention advantageously permits the use of flat radiators in a device according to German Patent No. 21 19 961 for the irradiation of liquids and/or gases.

The flat radiator has pronounced radiation characteristics by virtue of its flat oval cross-section with two narrow and two wide sides in each Maximum radiation is emitted by way of the wide sides, and only about 30% is emitted by way of the narrow sides.

According to the present invention, a set of flat radiators is arranged axially parallel to each other around the tubular body in such a way that the main axis of each flat radiator is oriented in the direction of the center axis of the tubular body. In this way, the maximum emission of the wide sides of the flat radiator takes place tangentially relative to the tubular body. Both this tangential flow of radiation and the flow of radiation averted from the tubular body are reversed into the latter by means of special reflectors.

Such an arrangement of the flat radiators significantly increases the efficiency of energy transfer in the tubular body as compared to the use of round radiators according to German Patent No. 21 19 961.

With specially shaped reflectors, for example parabolic or elliptic, it is possible to reduce the share of ultraviolet radiation re-reflected into the radiator to practically 0%. Taking into account the directed distribution of radiation and the angular dependence of emission and reflection, the arrangement of flat radiators and reflectors pursuant to the present invention achieves an output of 80 to 90% of the total emission into the fluid to be treated.

The arrangement of flat radiators and reflectors according to the present invention, furthermore, comprises contact cooling of the UV-radiators both directly by the fluid-conducting tubular body and indirectly by the reflector legs. For this purpose, the UV-radiators are arranged to abut against the tubular body on one narrow side, and against the reflector legs on the other narrow side. The reflectors themselves dissipate heat through contact with the tubular body.

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views:

FIG. 1 is a plan view, partly in cross-section, of an apparatus according to the present invention;

FIG. 2 is a view similar to that of FIG. 1, showing a different reflector;

FIG. 3 is a view similar to that of FIG. 1, showing a reflector with straight-extending reflector legs; and FIG. 4 is a view of a further embodiment of the present invention.

Now turning to the drawings, there is shown in FIG. 1 the apparatus according to the present invention, generally designated 10, comprising a tubular body 12 extending perpendicular to the plane of the drawing through which the liquid 14 to be sterilized flows. The jacket of tubular body 12 is formed of quartz and is thus permeable to UV-radiation.

Three flat radiators 16 are arranged externally around tubular body 12 with equal spacings between one another. Each flat radiator 16 has two narrow sides 18 and two wide sides 20. Also, a reflector 24 having two reflector legs 26 and 28 is associated with each flat radiator 16.

The flat radiators 16, which are arranged axially parallel to one another, are aligned in such a way that their main axis 22 extend radially relative to tubular body 12.

One of the narrow sides 18 of each radiator 16 abuts against tubular body 12, and the contact so established between flat radiator 16 and tubular body 12 results in contact cooling.

Reflector legs 26 and 28, with one of their ends, are in contact with tubular body 12 and with their second ends abut against outer narrow sides 18 of flat radiators 16. Thus contact cooling is also produced by the reflector legs 26 and 28.

The main direction of radiation of flat radiators 16 extends perpendicular to main axis 22, i.e., by far the major part of radiation exits from wide sides 20 tangentially relative to tubular body 12. With the help of reflector legs 26 and 28, both the tangential flow of radiation and the flow of radiation of outer narrow side 18, which is averted from tubular body 12, are reversed into tubular body 12.

While reflector legs 26 and 28 in FIG. 1 have an approximately elliptic shape, FIG. 2 shows an embodiment in which reflectors 24 have a parabolic configuration (for the sake of simplicity and clarity, FIG. 2 shows only one flat radiator 16 with a reflector 24). In the latter case, outer narrow side 18 of flat radiator 16 is not covered or engaged by reflector 24.

In the embodiment according to FIG. 3, reflector legs 26 and 28 are plane. As with the embodiment of FIG. 2, provision is made for contact cooling for flat radiator 16 and by means of reflector legs 26 and 28.

Tests have shown that with the apparatus according to the present invention, efficiency is enhanced to over 80% as compared to the maximum efficiency of 55% for the apparatus according to German Patent No. 21 19 961.

In FIG. 4 there is shown yet another embodiment of the present invention having a plurality of flat radiators 30 arranged in series with spacing there between. In this case, therefore, a tubular body according to FIGS. 1 to 3 is dispensed with and the surface 42 of a medium is subjected to UV-radiation 40.

The main axis 32 of the flat UV-radiators 30 are aligned perpendicular to surface 42.

In a manner comparable with the arrangements shown in FIGS. 1 to 3, a reflector 44 is associated with each flat UV-radiator with its wide sides 34 and narrow sides 36. Provision is made for a common holding device 38 for the mechanical fastening of these elements.

Reflectors 44 cause the UV-radiation 40 exiting from wide sides 34 of flat UV-radiators 30 to be reversed and reflected in such a way that it strikes surface 42 approximately in a vertical line.

This last embodiment is not limited to the sterilization of media, but can be applied also for other purposes, for example, in tanning systems, in which UV-light is produced for skin tanning.

While several embodiments of the present invention have been shown and described, it will be obvious that many changes and modifications may be made thereunto without departing from the spirit and scope of the invention.

What is claimed is:

1. Apparatus for irradiating media with UV-light, comprising a tubular body formed of UV-permeable material, the medium to be irradiated passing through said tubular body, and at least two flat UV-radiators with reflectors arranged externally to said tubular body and having parallel axes, said UV-radiators having oblong, flat oval cross-sections with wide and narrow sides.

2. The apparatus as defined in claim 1, wherein the main axis of the UV-radiators are directed at the axis of the tubular body.

3. The apparatus as defined in claim 2, wherein said UV-radiators, having their narrow sides facing the tubular body, abut against said tubular body.

4. The apparatus as defined in claim 3, wherein each said reflector is formed having two reflector legs whose ends averted from the tubular body are in contact with the respective flat UV-radiator.

5. The apparatus as defined in claim 4, wherein said reflector legs, with their ends facing the tubular body, abut against said tubular body.

6. The apparatus as defined in claim 5, wherein said reflectors have a parabolic shape.

7. The apparatus as defined in claim 5, wherein said reflectors are in the form of a conic section.

8. The apparatus as defined in claim 5, wherein said reflectors have a planar shape.

9. Apparatus for irradiating media with UV-light, comprising a plurality of UV-light sources arranged adjacent to each other in series, said UV-light sources each being formed by a flat UV-radiator having an oblong, flat cross section with wide and narrow sides and a main axis, said main axis of each flat UV-radiator being arranged perpendicular to the surface of the medium, and a reflector directing the UV-radiation vertically at the medium is associated with each flat UV-radiator.

* * * * *